(12) United States Patent
Zheng et al.

(10) Patent No.: US 8,173,974 B2
(45) Date of Patent: May 8, 2012

(54) METHOD OF INDIRECT EMISSION BY NANO-MATERIALS

(75) Inventors: Yan Zheng, Shanghai (CN); Jingyu Bian, Shanghai (CN); Shufan Geng, Shanghai (CN); Ruifu Yang, Shanghai (CN); Lei Zhou, Shanghai (CN); Huijie Huang, Shanghai (CN); Youbao Zhang, Shanghai (CN); Lihua Huang, Shanghai (CN)

(73) Assignee: Shanghai Keyan Phosphor Technology Co., Ltd., Pudong District, Shanghai (CN)

( * ) Notice: Subject to any disclaimer, the term of this patent is extended or adjusted under 35 U.S.C. 154(b) by 144 days.

(21) Appl. No.: 12/869,788

(22) Filed: Aug. 27, 2010

(65) Prior Publication Data

US 2011/0057118 A1 Mar. 10, 2011

(30) Foreign Application Priority Data

Sep. 8, 2009 (CN) .......................... 2009 1 0195288

(51) Int. Cl.
*G01J 1/58* (2006.01)

(52) U.S. Cl. ..................................................... 250/459.1
(58) Field of Classification Search ................ 250/459.1
See application file for complete search history.

(56) References Cited

U.S. PATENT DOCUMENTS

| | | | | |
|---|---|---|---|---|
| 3,707,641 | A | * | 12/1972 | Thornton ...................... 313/487 |
| 6,686,691 | B1 | * | 2/2004 | Mueller et al. ................ 313/503 |
| 2005/0179364 | A1 | * | 8/2005 | Murazaki ...................... 313/498 |

* cited by examiner

*Primary Examiner* — David Porta
*Assistant Examiner* — Marcus Taningco

(57) ABSTRACT

A method of indirect emission by nano-materials includes providing an infrared up-conversion phosphor 1 (weight ratio) and a long-wave ultraviolet phosphor 0.01-10 (weight ratio); treating both surfaces of the infrared up-conversion phosphor and the long-wave ultraviolet phosphor; mixing the infrared up-conversion phosphor and the long-wave ultraviolet phosphor; exciting the infrared up-conversion phosphor by a near-infrared laser with a wavelength of 980 mn to emit blue light as a secondary excitation lightsource; exciting the long-wave ultraviolet phosphor by the blue light to emit a visible light. Biological reactions can be conveniently detected by detecting the visible light.

20 Claims, No Drawings

METHOD OF INDIRECT EMISSION BY NANO-MATERIALS

BACKGROUND OF THE PRESENT INVENTION

1. Field of Invention

The present invention relates to detection field, and more particularly to biological detection.

2. Description of Related Arts

Recently, the up-conversion phosphor has been using as a biomarker in biological sciences to a certain extent. Its unique up-conversion emission feature makes the biological detection technology has the advantages of good stability, high sensitivity, easy and fast operation, qualitative and quantitative analysis, etc. However, this traditional direct excitation and emission requires that the detection process must adopt solid phase materials or other technical means to completely separate the free biomarkers which do not react with the detector, otherwise, any residual free biomarker will be a source of false positive signal. In addition, the traditional mode can not detect the extent of microbe reaction by detecting signal intensities of the biomarkers in above mixed system. The application methods of the up-conversion phosphor have been introduced in the Chinese patents: Pat. No. 200410034105.5, Pat. No. 200410034104.0, and Pat. No. 200420049580.5.

Most existing preparations of blue-emitting up-conversion phosphor are body materials with larger particles or microcrystal ceramic glassy state materials, although both of them have high luminous efficiency, neither can be used in biological field. On the other hand, the existing synthetic technologies of nanometer have to add fluxing agent for improving luminous efficiency, which results in high content of impurities. Chinese patents: Pat. No. 01138927.3, Pat. No. 01138920.6, Pat. No. 200410017067.2, and Pat. No. 200510123022.8 have revealed above expatiation.

SUMMARY OF THE PRESENT INVENTION

An object of the present invention is to provide a method of indirect emission by nano-materials, in which, firstly, excite a kind of blue-emitting infrared up-conversion phosphor to emit blue light by a near-infrared laser, then excite another long-wave ultraviolet phosphor indirectly by the blue light within a specific distance. By using this indirect transmission of energy, detections can achieve easily and fast qualitative and quantitative analysis by simply mixing the sample solution with the two materials instead of follow-up separation. Meanwhile, during whole detection, researchers can detect the visual light at any time, so as to monitor the speed and extent of the reaction to meet different requirements of applied research and basic research. , Without any separation, Accordingly, in order to accomplish the above objects, the present invention provides a method of indirect emission by nano-materials comprising: providing an infrared up-conversion phosphor 1 (weight ratio) and a long-wave ultraviolet phosphor 0.01-10 (weight ratio); treating the surface of the infrared up-conversion phosphor and the long-wave ultraviolet phosphor; mixing the infrared up-conversion phosphor and the long-wave ultraviolet phosphor; exciting the infrared up-conversion phosphor by a near-infrared laser with a wavelength of 980 mn to emit blue light with a wavelength of 440-480 mn as a secondary excitation lightsource; exciting the long-wave ultraviolet phosphor by the blue light to emit visible light with a wavelength of 490-650 nm, wherein an mixing ratio of the infrared up-conversion phosphor and the long-wave ultraviolet phosphor depends on the luminous efficiency and type of the long-wave ultraviolet phosphor. Due to the long-wave ultraviolet phosphor excited by the blue light, therefore, the smaller particle size of the long-wave ultraviolet phosphor is, the higher luminous efficiency is obtained.

A method for preparing the infrared up-conversion phosphor as recited above comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared phosphor which can emits blue light under excitation, wherein a range of particle size of the obtained infrared phosphor is 70-800 nm. The sintering process prepared in argon can effectively prevent the preparing materials from oxidation, so as to improve luminous efficiency and control color purity. Meanwhile, the sintering process conducted in low temperature can inhibit the growth of particles.

The long-wave ultraviolet phosphor as recited above is a plurality of stable monochromatic micro-particles, with an absorption spectrum of 440 nm-480 nm and an emission spectrum of 490-650 nm.

Furthermore, the infrared up-conversion phosphor and the long-wave ultraviolet phosphor as recited above are respectively treated their surface by sol-gel method. After treatment, their surface applies to link with different chemical substance, and can be used for biological detection.

Alternatively, the infrared up-conversion phosphor and the long-wave ultraviolet phosphor do not be mixed together, instead, they are separately prepared to biological detection reagent layers.

These and other objectives, features, and advantages of the present invention will become apparent from the following detailed description, and the appended claims.

DETAILED DESCRIPTION OF THE PREFERRED EMBODIMENT

A method for preparing a blue-emitting infrared up-conversion phosphor which emits blue light under excitation comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared up-conversion phosphor which emits blue light under excitation in form of micro-particles. Here, a range of particle size of the obtained infrared up-conversion phosphor is 70-800 nm. After excited by a near-infrared laser with a wavelength of 980 nm, the obtained infrared up-conversion phosphor can emit blue light with a wavelength in range of 440-480 nm.

It is worth to mention that when the sintering temperature blew 350° C. and sintering time less then 2 hours, an the obtained infrared phosphor has an average diameter below 100 nm, and has a weaker luminous intensity; while when the sintering temperature above 400° C. and sintering time larger then 4 hours, the obtained infrared phosphor is of blocky structure, and has a stronger luminous intensity, after grinding, the average diameter of the obtained infrared phosphor is above 700 nm. It is worth to point that only the sintering process is protected in argon, an emission spectrum of the obtain infrared phosphor can reach to less then 470 nm, while the sintering process is exposed to the air, the emission spectrum of the obtain infrared phosphor will be above 470 nm.

When the emission spectrum of the infrared phosphor is less then 470 nm, and the infrared phosphor has a higher luminous efficiency, a luminous efficiency of indirect-conversion exciting a long-wave ultraviolet phosphor can be improved greatly.

Here, the phosphor which is excited by ultraviolet at long-wave band is known as ultraviolet phosphor (e.g., organic rhodamine B, 7-amino-4-methyl coumarin, inorganic YAG phosphor), which is either organic or inorganic phosphor, and is stable monochromatic micro-particles, and can not be excited by the near-infrared laser with a wavelength of 980 nm. When an absorption spectrum of the ultraviolet phosphor is 440 nm-480 nm, the ultraviolet phosphor can emit luminescence efficiently, and its emission spectrum is 490-650 nm. So, the above features of the ultraviolet phosphor avoid overlapping with the up-conversion phosphor in blue emission region. Therefore, using the blue-emitting infrared up-conversion phosphor and the long-wave ultraviolet phosphor as detecting materials applies to identification and analysis of spectrum by automatic detection apparatus, and also applies to directly visual judgment.

In existing technology, the synthesis and use technology of the long-wave ultraviolet phosphor is mature, which makes the ultraviolet phosphor has wider range in particle size and control scope. When the particle size is smaller, the mixing ratio with the infrared phosphor should be reduced. For example, a kind of organic long-wave ultraviolet phosphor has so high luminous efficiency that its molecules emit independently. The organic long-wave ultraviolet phosphor has widely used in biological engineering field.

The infrared up-conversion phosphor which emits blue light under excitation and the long-wave ultraviolet phosphor as recited above, perferably, are respectively treated their surface by sol-gel method. In the present invention, the infrared up-conversion phosphor and the ultraviolet phosphor are respectively treated by tetraethoxysilane (TEOS), which is formed $SiO_2$ package film after hydrolysis. After treatment, the emission particles of the infrared up-conversion phosphor and the ultraviolet phosphor are more diffuse, easy to be mixed and easy to be linked with organic bioactive molecules.

A method of indirect emission by nano-materials comprises: providing the infrared up-conversion phosphor 1 (weight ratio) and the long-wave ultraviolet phosphor 0.01-10 (weight ratio); mixing the infrared up-conversion phosphor and the long-wave ultraviolet phosphor; exciting the infrared up-conversion phosphor by the near-infrared laser with a wavelength of 980 mn to emit blue light with a wavelength of 440-480 mn as a secondary excitation lightsource; exciting the long-wave ultraviolet phosphor by the blue light to emit visible light with a wavelength of 490-650 nm.

Alternatively, the infrared up-conversion phosphor and the long-wave ultraviolet phosphor do not be mixed together, instead, the infrared up-conversion phosphor and the long-wave ultraviolet phosphor are separately prepared to biological detection reagent layers. Using chromatography, according to a certain proportion, assembly the biological detection reagent layers of the infrared up-conversion phosphor and the long-wave ultraviolet phosphor within a kit.

First Embodiment

The method for preparing blue-emitting infrared up-conversion phosphor comprises: providing 90 g $YF_3$ and 10 g $GdF_3$; adding into 45 g $YbF_3$; adding into 13 g $TmF_3$; sintering the fluoride mixture in argon at 400° C. for 2 hours to obtain the blue-emitting infrared phosphor which emits blue light with a wavelength of 450 nm under excitation by a near-infrared laser with a wavelength of 980 mn, wherein an average particle size of the blue-emitting infrared phosphor is 100 nm; soaking the blue-emitting infrared phosphor in 10% tetraethoxysilane (TEOS) solution for 3 hours; taking the blue-emitting infrared phosphor out of the tetraethoxysilane (TEOS) solution and drying the infrared up-conversion phosphor and the blue-emitting infrared phosphor.

The method of indirect emission by nano-materials comprises: providing 1 g infrared up-conversion phosphor as prepared above, and 0.1 g organic rhodamine B as long-wave ultraviolet phosphor; mixing the infrared up-conversion phosphor and the organic rhodamine B; exciting the infrared up-conversion phosphor by the near-infrared laser with a wavelength of 980 mn to emit blue light with a wavelength of 440 mn as a secondary excitation lightsource; exciting the organic rhodamine B by the blue light to emit visible light with a wavelength of 630 nm.

Second Embodiment

The method for preparing blue-emitting infrared up-conversion phosphor comprises: providing 100 g $YF_3$; adding into 50 g $YbF_3$; adding into 20 g $TmF_3$; sintering the fluoride mixture in argon at 450° C. for 5 hours to obtain the blue-emitting infrared phosphor; grinding the blue-emitting infrared phosphor to obtain particles with an average diameter of 800 nm, which can emits blue light with a wavelength of 470 nm under excitation by a near-infrared laser with a wavelength of 980 mn; soaking the blue-emitting infrared phosphor in 10% tetraethoxysilane (TEOS) solution for 3 hours; taking the blue-emitting infrared phosphor out of the tetraethoxysilane (TEOS) solution and drying the infrared up-conversion phosphor and the blue-emitting infrared phosphor.

The method of indirect emission by nano-materials comprises: providing 1 g infrared up-conversion phosphor as prepared above, and 1 g inorganic YAG phosphor as long-wave ultraviolet phosphor; mixing the infrared up-conversion phosphor and the inorganic YAG phosphor; exciting the infrared up-conversion phosphor by the near-infrared laser with a wavelength of 980 mn to emit blue light with a wavelength of 470 mn as a secondary excitation lightsource; exciting the inorganic YAG phosphor by the blue light to emit visible light with a wavelength of 555 nm.

A method of detection by using the indirect emission, comprises: adding a first bioactive molecule which is marked by the blue-emitting infrared up-conversion phosphor, and a second bioactive molecule which is marked by the long-wave ultraviolet phosphor into an sample solution to assist detection; combining the first bioactive molecule and the second bioactive molecule respectively with objective tested substances in the sample solution to form an first-objective tested substance and an second-objective tested substance, wherein due to these combinations, a distance between the blue-emitting infrared up-conversion phosphor and the long-wave ultraviolet phosphor is within the specific distance; exciting the first-objective tested substance by the near-infrared laser with a wavelength of 980 mn to emit blue light with a wavelength of 440-480 mn as a secondary excitation lightsource; exciting the second-objective tested substance by the blue light to emit visible light with a wavelength of 490-650 nm; detecting the sample solution by detecting the visible light.

Therefore, the visual light indirectly excited can be indicative of specific biological reactions in the sample solution.

The beneficial effects of the present invention are illustrated as follows: firstly, the indirect emission mode between the infrared up-conversion phosphor and the long-wave ultraviolet phosphor makes a simply mixing operation instead of complicated separation in detection process, so as to simplify operation process and reduce time.

Secondly, the indirect emission mode between the infrared up-conversion phosphor and the long-wave ultraviolet phosphor makes the visual light directly shows the speed and the extent of the microbe. Therefore, this method applies to analyze the interaction between protein-protein, protein-nucleic acid, nucleic acid-nucleic acid, etc.

One skilled in the art will understand that the embodiment of the present invention as described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of indirect emission by nano-materials, comprising: providing an infrared up-conversion phosphor, which emits a blue light under excitation; providing a long-wave ultraviolet phosphor, wherein a weight ratio of the infrared up-conversion phosphor to the long-wave ultraviolet phosphor is 1:0.01-10; exciting the infrared up-conversion phosphor by an near-infrared laser with a wavelength of 980 nm to emit a blue light with as a secondary excitation lightsource; exciting the long-wave ultraviolet phosphor by the blue light to emit a visible light.

2. The method of indirect emission by nano-materials, as recited in claim 1, further comprising mixing the infrared up-conversion phosphor and the long-wave ultraviolet phosphor together.

3. The method of indirect emission by nano-materials, as recited in claim 1, further comprising preparing the infrared up-conversion phosphor and the long-wave ultraviolet phosphor separately into a biological detection reagent layer; assembling the biological detection reagent layers of the infrared up-conversion phosphor and the long-wave ultraviolet phosphor within a kit.

4. The method of indirect emission by nano-materials, as recited in claim 1, wherein a method for preparing the infrared up-conversion phosphor which emits blue light under excitation comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared up-conversion phosphor.

5. The method of indirect emission by nano-materials, as recited in claim 2, wherein a method for preparing the infrared up-conversion phosphor which emits blue light under excitation comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared up-conversion phosphor.

6. The method of indirect emission by nano-materials, as recited in claim 3, wherein a method for preparing the infrared up-conversion phosphor which emits blue light under excitation comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared up-conversion phosphor.

7. The method of indirect emission by nano-materials, as recited in claim 5, wherein the long-wave ultraviolet phosphor is a plurality of stable monochromatic micro-particles, with an absorption spectrum of 440 nm-480 nm and an emission spectrum of 490-650 nm.

8. The method of indirect emission by nano-materials, as recited in claim 6, wherein the long-wave ultraviolet phosphor is a plurality of stable monochromatic micro-particles, with an absorption spectrum of 440 nm-480 nm and an emission spectrum of 490-650 nm.

9. The method of indirect emission by nano-materials, as recited in claim 7, wherein the long-wave ultraviolet phosphor is organic rhodamine B, 7-amino-4-methyl coumarin, or inorganic YAG phosphor.

10. The method of indirect emission by nano-materials, as recited in claim 8, wherein the long-wave ultraviolet phosphor is organic rhodamine B, 7-amino-4-methyl coumarin, or inorganic YAG phosphor.

11. The method of indirect emission by nano-materials, as recited in claim 7, further comprising treating both surfaces of the infrared up-conversion phosphor and the long-wave ultraviolet phosphor respectively by a sol-gel method.

12. The method of indirect emission by nano-materials, as recited in claim 8, further comprising treating both surfaces of the infrared up-conversion phosphor and the long-wave ultraviolet phosphor respectively by a sol-gel method.

13. The method of indirect emission by nano-materials, as recited in claim 11, wherein the sol-gel method comprises soaking the infrared up-conversion phosphor and the long-wave ultraviolet phosphor in 10% tetraethoxysilane solution for 3 hours; taking the blue-emitting infrared phosphor out of the tetraethoxysilane solution and drying the infrared up-conversion phosphor and the blue-emitting infrared phosphor.

14. The method of indirect emission by nano-materials, as recited in claim 12, wherein the sol-gel method comprises soaking the infrared up-conversion phosphor and the long-wave ultraviolet phosphor in 10% tetraethoxysilane solution for 3 hours; taking the blue-emitting infrared phosphor out of the tetraethoxysilane solution and drying the infrared up-conversion phosphor and the blue-emitting infrared phosphor.

15. A method of detecting a sample by using of indirect emission, comprising: adding a first bioactive molecule which is marked by the blue-emitting infrared up-conversion phosphor, and a second bioactive molecule which is marked by the long-wave ultraviolet phosphor into the sample to assist detection; combining the first bioactive molecule and the second bioactive molecule respectively with objective tested substances in the sample to form an first-objective tested substance and an second-objective tested substance; exciting the first-objective tested substance by an near-infrared laser with a wavelength of 980 mn to emit a blue light as a secondary excitation lightsource; exciting the second-objective tested substance by the blue light to emit a visible light; detecting the sample by detecting the visible light.

16. The method of detection by using of indirect emission, as recited in claim 15, wherein a method for preparing the blue-emitting infrared up-conversion phosphor which emits blue light under excitation comprises: providing a fluoride mixture which comprises an element selected from the group consisting of Y, Gd, and La; adding into $YbF_3$ which is 45-50 percent by weight of the fluoride mixture; adding into $TmF_3$ which is 12-25 percent by weight of the fluoride mixture; sintering the fluoride mixture in argon at 300-450° C. for 1-6 hours to obtain the infrared up-conversion phosphor.

17. The method of detection by using of indirect emission, as recited in claim 16, wherein the long-wave ultraviolet phosphor is a plurality of stable monochromatic micro-particles, with an absorption spectrum of 440 nm-480 nm and an emission spectrum of 490-650 nm.

18. The method of detection by using of indirect emission, as recited in claim 17, wherein the long-wave ultraviolet phosphor is organic rhodamine B, 7-amino-4-methyl coumarin, or inorganic YAG phosphor.

19. The method of detection by using of indirect emission, as recited in claim 17, wherein both surfaces of the infrared up-conversion phosphor and the long-wave ultraviolet phosphor are treated respectively by a sol-gel method.

20. The method of detection by using of indirect emission, as recited in claim 19, wherein the sol-gel method comprises soaking the infrared up-conversion phosphor and the long-wave ultraviolet phosphor in 10% tetraethoxysilane solution for 3 hours; taking the blue-emitting infrared phosphor out of the tetraethoxysilane solution and drying the infrared up-conversion phosphor and the blue-emitting infrared phosphor.

* * * * *